US00PP35152P2

(12) United States Plant Patent
Strode et al.

(10) Patent No.: US PP35,152 P2
(45) Date of Patent: May 2, 2023

(54) ***ALOCASIA* PLANT NAMED 'AS12-1'**

(50) Latin Name: ***Alocasia* hybrid**
Varietal Denomination: AS12-1

(71) Applicants: Ty R. Strode, Apopka, FL (US); Karen G. Steinkamp, Apopka, FL (US)

(72) Inventors: Ty R. Strode, Apopka, FL (US); Karen G. Steinkamp, Apopka, FL (US)

(73) Assignee: Agri-Starts, Inc., Apopka, FL (US)

( * ) Notice: Subject to any disclaimer, the term of this patent is extended or adjusted under 35 U.S.C. 154(b) by 0 days.

(21) Appl. No.: 17/803,796

(22) Filed: Nov. 28, 2022

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Plant Novelty Rights, LLC; James R. Holm

(57) ABSTRACT

A new and distinct *Alocasia* plant named 'AS12-1' particularly distinguished by unique large and broadly ovate to cordate shaped leaves with undulating leaf margins that fold downwards giving the leaf an overall scalloped appearance, moderate olive-green color on the upper side of mature leaves and unique dark greyish purple color on the underside of mature leaves.

5 Drawing Sheets

Figure 1:
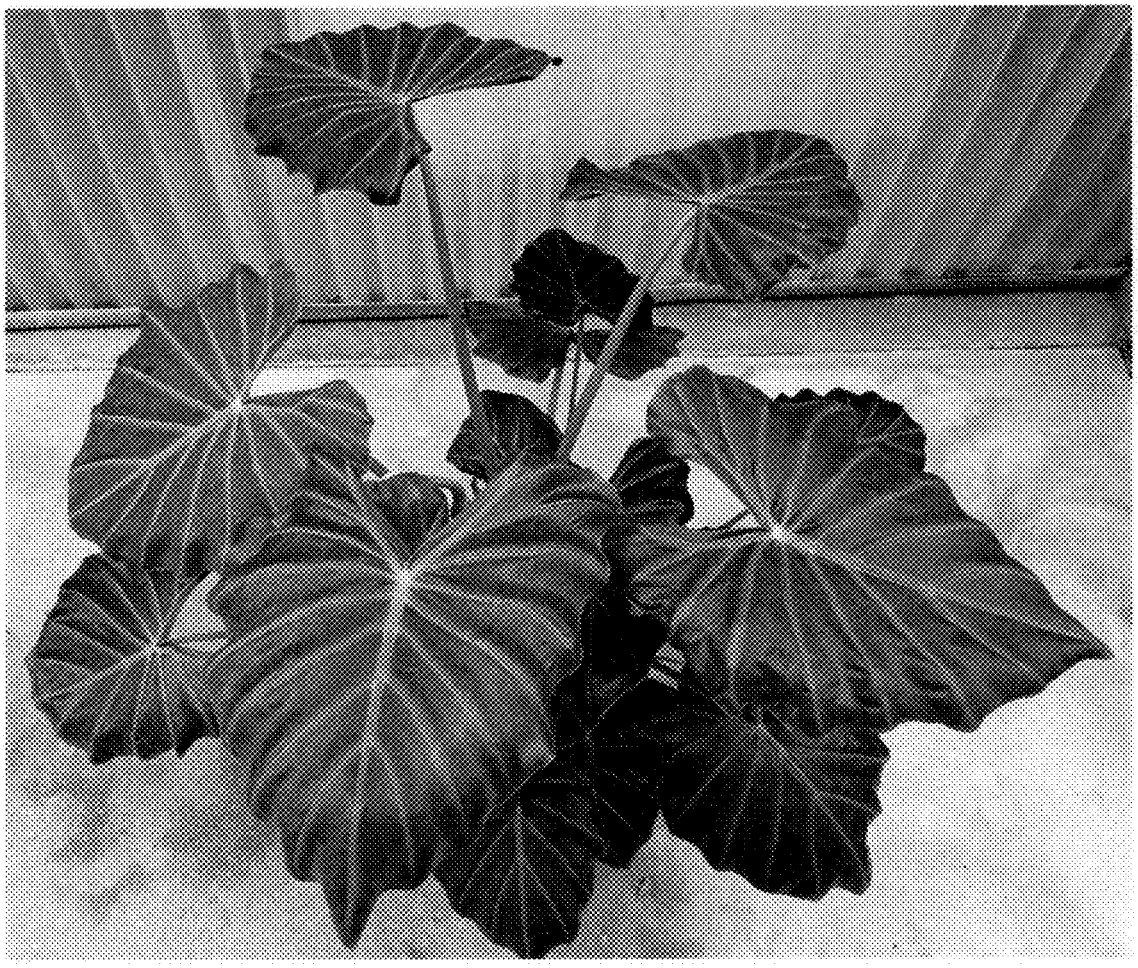

Genus and species: *Alocasia* hybrid.
Variety denomination: 'AS12-1'.

BACKGROUND OF THE NEW PLANT

The present invention comprises a new and distinct interspecific hybrid plant of *Alocasia*, hereinafter referred to by its cultivar name 'AS12-1'.

The new cultivar was derived from a controlled breeding program conducted by the inventors at a nursery in Mount Dora, Fla. The overall purpose of the breeding program is to make new selections of *Alocasia* plants with unique foliage that are durable with a good growth rate in Florida. 'AS12-1' is the product of a controlled cross made by the inventors in April 2021 between the hybrid *Alocasia* plant named 'Calidora' (unpatented) as the female parent and the species *Alocasia amazonica* as the male parent. 'AS12-1' was selected by the inventors in the spring of 2022 as a single unique plant in Mount Dora, Fla. from amongst progeny plants derived from said cross.

The new cultivar was selected based on its distinctive coloration, unique scalloped leaf appearance and durability as compared to other commercially available *Alocasia* cultivars. 'AS12-1' was first reproduced asexually by vegetative rhizome divisions in August 2022 in Mount Dora, Fla. Asexual propagation by vegetative rhizome divisions of the new cultivar has shown that the unique features of the new cultivar are stable and reproduce true-to-type in successive generations.

Plant Breeder's Rights for this variety have not been applied for. 'AS12-1' has not been made publicly available or sold anywhere in the world prior to the effective filing date of this application.

SUMMARY OF THE INVENTION

The new *Alocasia* cultivar has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Alocasia* cultivar. The combination of these characteristics distinguishes 'AS12-1' as a new and distinct variety of *Alocasia:*

1. Large and broadly ovate to cordate shaped leaves;
2. Undulating leaf margins that fold downwards giving the leaf an overall scalloped appearance;
3. Moderate olive-green color on the upper side of mature leaves; and
4. Unique dark greyish purple color on the underside of mature leaves.

DESCRIPTION OF THE PHOTOGRAPHS

This new *Alocasia* cultivar is illustrated by the accompanying-colored photographs which show the overall appearance and distinct characteristics of the plant. The colors shown are as true as can be reasonably obtained by conventional photographic procedures. The photographs are of a 1-year-old plant grown in a 3-gallon container under 60 to 90 percent shade in a ploy covered greenhouse in Mount Dora, Fla. Colors in the photographs may differ slightly from the color values cited in the botanical description which accurately describes the colors of the new variety.

FIG. 1. shows a top view of the overall plant form and foliage of 'AS12-1'.

Figure 2:
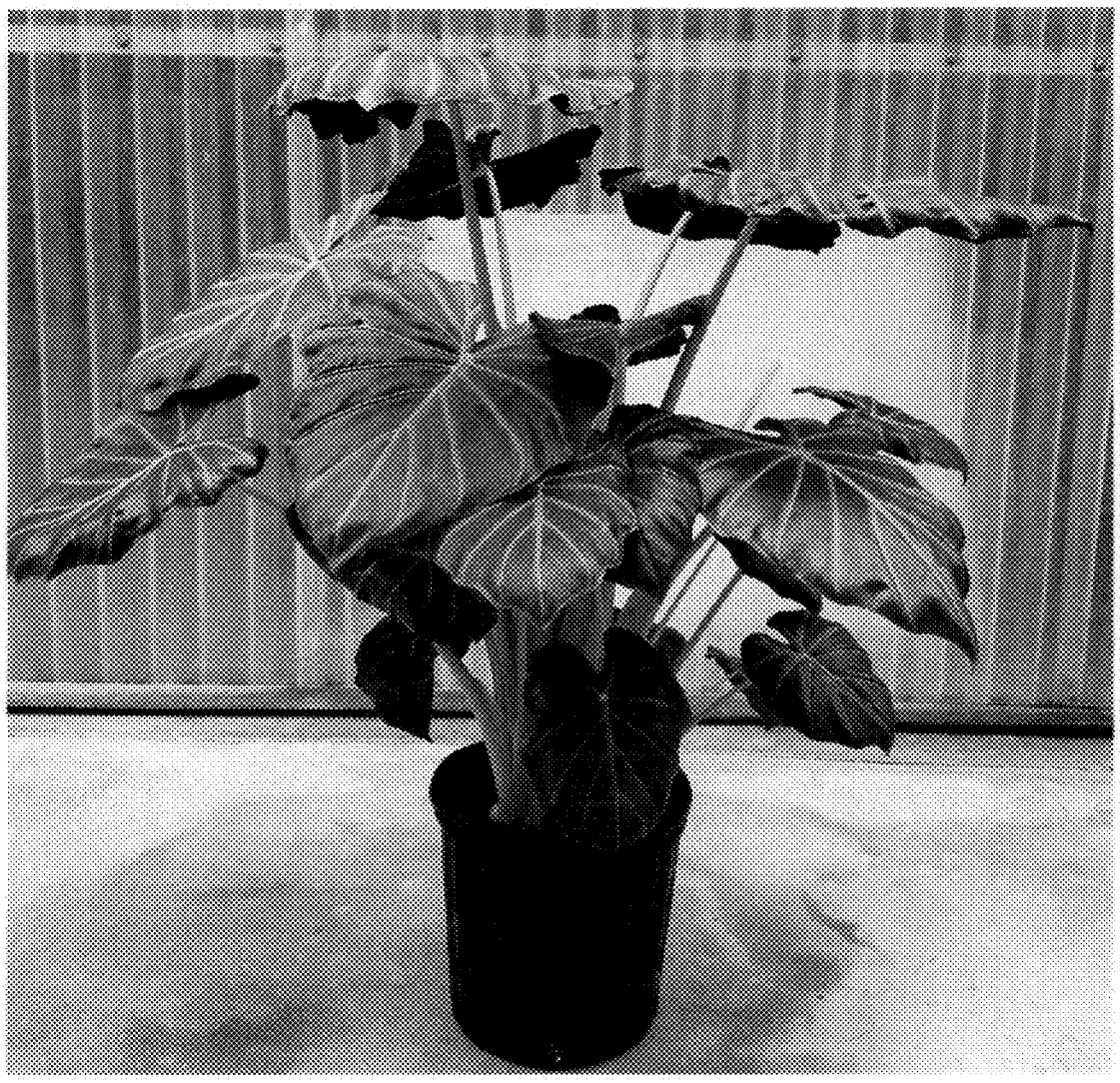

FIG. 2. shows a side view of the overall plant form and foliage of 'AS12-1'.

Figure 3:
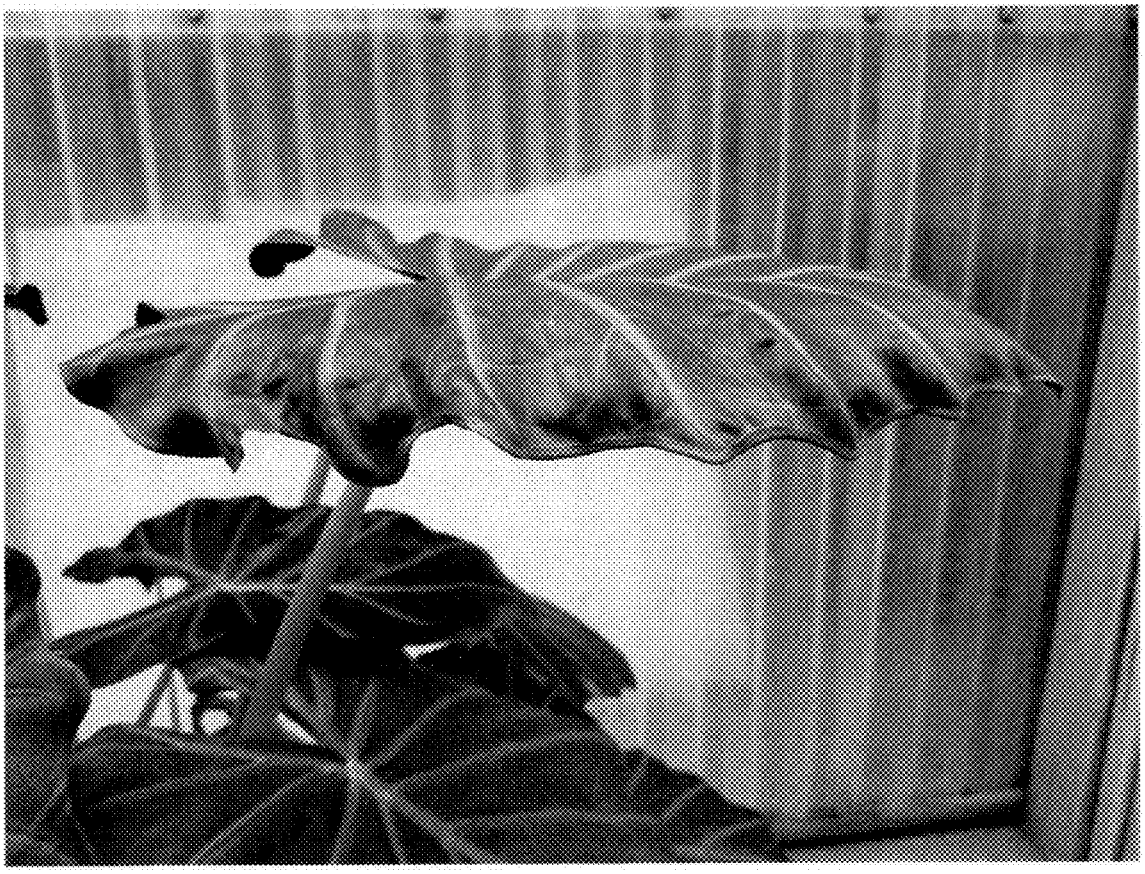

FIG. 3. shows a side view close up of a mature leaf of 'AS12-1'.

Figure 4:
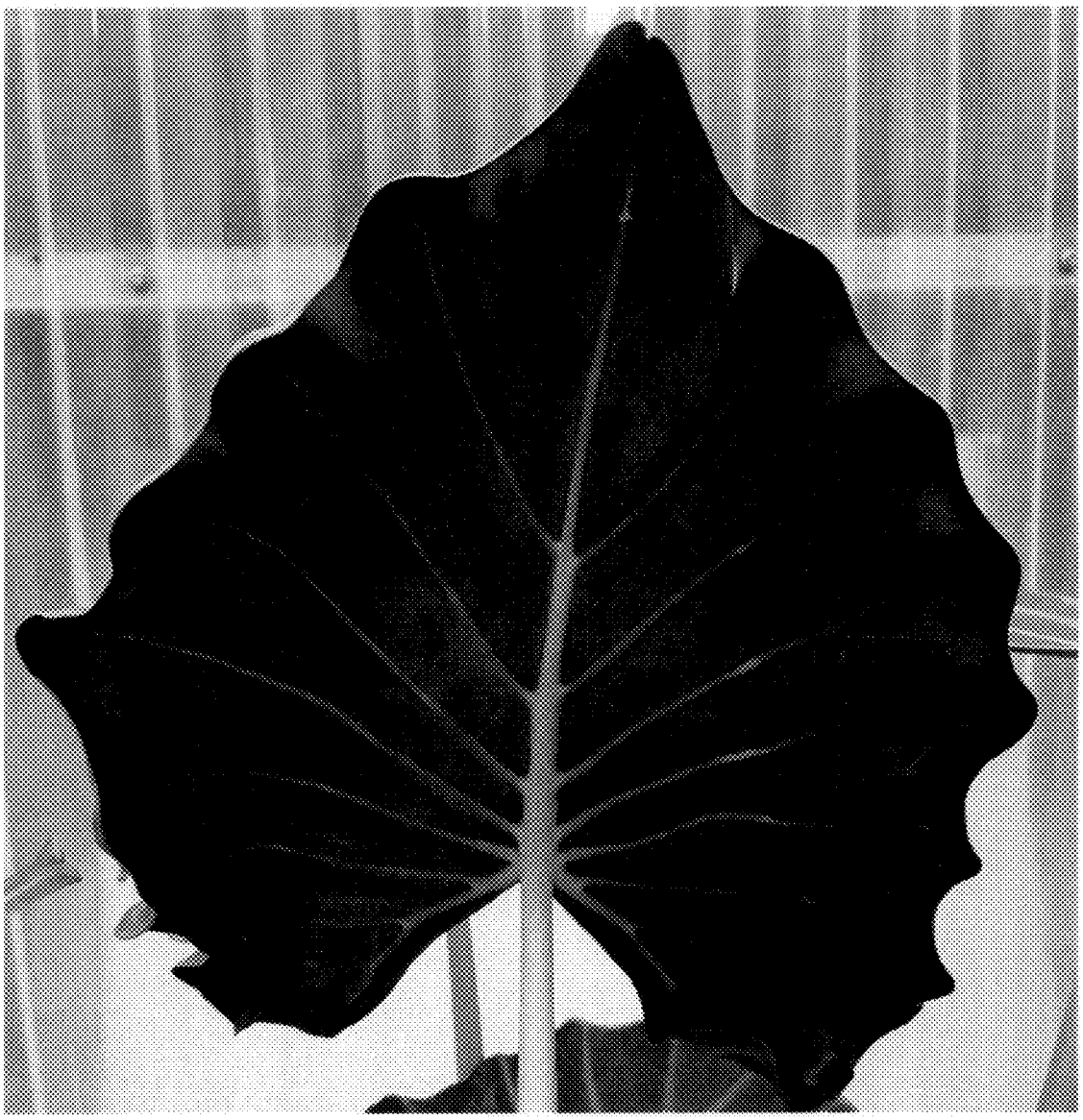

FIG. 4. shows a closeup of the abaxial surface of a mature leaf of 'AS12-1'.

Figure 5:
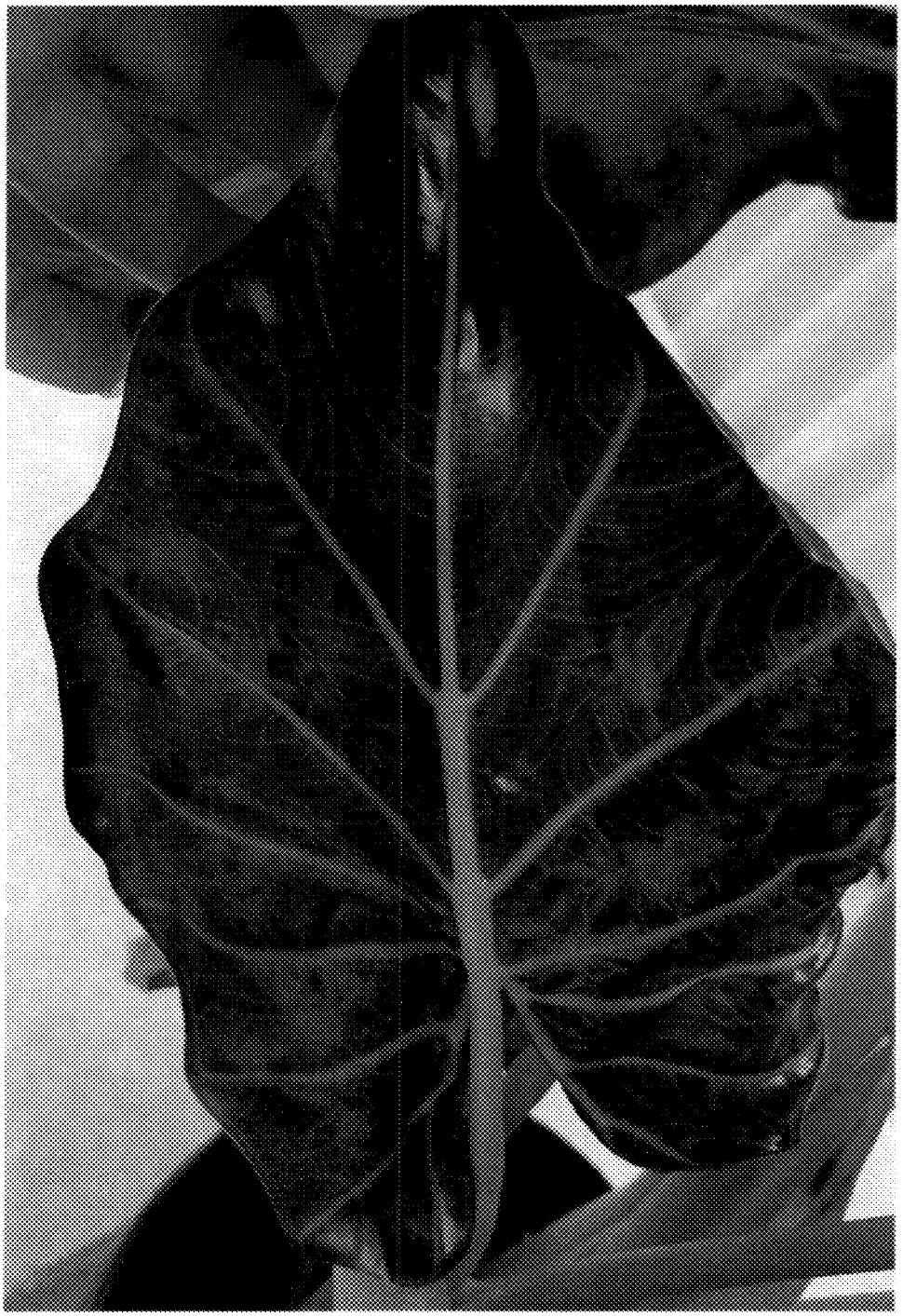

FIG. 5. shows a closeup of the abaxial surface of a juvenile leaf of 'AS12-1'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown under 60 to 90 percent shade in a poly covered greenhouse in Mount Dora, Fla. Detailed descriptions were taken in October to November 2022 from a 1-year-old plant grown in a 3-gallon container. Measurements and numerical values represent averages of typical plant types.

DETAILED BOTANICAL DESCRIPTION

Classification:

*Family*.—Araceae.

*Botanical*.—*Alocasia* hybrid.

*Common*.—*Alocasia* or Elephant Ear.

*Denomination*.—'AS12-1'.

General description:

*Plant type*.—Tropical perennial.

*Growth habit*.—Upright and becoming outwardly arching with development.

*Height from soil level to top of foliar plane*.—Approximately 70.0 cm.

*Plant spread*.—Approximately 86.0 cm.

*Number of basal shoots per plant*.—4.

*Primary stem*.—Rhizomatous, approximately 7.6 cm in diameter at the base.

*Growth rate*.—Moderate.

*Propagation type*.—Vegetative rhizome divisions.

*Roots*.—Thick, fleshy and fibrous, colored 156D (yellowish white).

Foliage description:

*Quantity of leaves per plant*.—Primary shoot: 6. Young axillary shoots: 5.

*Arrangement*.—Alternate.

*Attachment*.—Petiolate.

*Division*.—Simple.

*Lamina*.—Shape: Broadly ovate to cordate. Length: Approximately 30.0 cm to 33.0 cm when measured along the center axis of the foliar plane. Width: Approximately 20.3 cm at the widest point above the lobes. Orientation: Initially held vertically and becoming horizontal when mature. Appearance: Undulating margins that fold downwards giving the leaf an overall scalloped appearance. Apex: Acuminate when developing, becoming cuspidate when developed. Base: Deeply lobed, lobes about 10.0 cm to 12.0 cm in width and about 7.5 cm in depth. Margins: Undulate. Texture and luster, adaxial surface: Slightly rugose, shiny and becoming more matt on mature leaves. Texture and luster, abaxial surface: Smooth, glabrous and glossy. Venation pattern: Pinnate, one primary vein (midvein) and approximately 14 secondary veins with numerous veinlets appearing in a netted pattern. Color: Juvenile foliage, adaxial surface: Interveinal areas: NN137B (greyish olive green). Primary vein: N144C (strong yellow green). Secondary veins: N144C (strong yellow green), darkening towards the margins, 144B (strong yellow green). Veinlets: N144D (strong yellow green). Juvenile foliage, abaxial surface: Interveinal areas: 187A (dark red). Primary vein: 145A (strong yellow green). Secondary veins: 145A (strong yellow green) close to the primary vein, darkening towards the margins and tinged with N187C (purplish grey). Veinlets: Tinged with N187D (light purplish grey). Mature foliage, adaxial surface: Interveinal areas: NN137A (moderate olive green). Basal notch: 145B (light yellow green). Primary vein: N144D (strong yellow green) near the basal notch, becoming 137C (moderate yellowish green) towards the leaf margin. Secondary veins: 137C (moderate yellowish green). Veinlets: Inconspicuous. Mature foliage, abaxial surface: Interveinal areas: N186B (dark greyish purple). Primary vein: 145C (light yellow green). Secondary veins: 145C (light yellow green) near the primary vein, tinged with N186B (dark greyish purple) towards the leaf margin with a prominent notch of 145C (light yellow green) about halfway towards the leaf margin. Veinlets: Inconspicuous.

*Petioles*.—Strength: Flexible. Aspect: Initially upright and straight and becoming more arching with development. Length: Approximately 53.0 cm to 55.0 cm. Diameter: Distally: Approximately 1.0 cm. Proximally: Approximately 9.0 cm. Texture and luster: Glabrous and glossy. Color: Close to 145A (strong yellow green) with mottled streaks of 145D (light yellow green). Wing length: Approximately 17.7 cm. Wing width: Approximately 9.0 cm at the base. Wing texture and luster (both inner and outer surfaces): Glabrous and glossy. Wing color (both inner and outer surfaces): 145C to 145D (light yellow green).

Inflorescence:

*Type*.—Spadix surrounded by a spathe, male portion held above female portion.

*Peduncle*.—Length: Up to 15.0 cm. Diameter: 0.6 cm, widening towards the base of the spadix, 1.3 cm. Color: 145A (strong yellow green).

*Spathe*.—Shape: Wedge-shaped above female zone, elliptic in shape surrounding female zone. Margin: Entire. Length: 11.4 cm above female zone, 3.2 cm surrounding female zone. Width: 3.2 cm above female zone, 2.5 cm surrounding female zone. Color: 145A (strong yellow green) above female zone when opening and fully opened, fading to 162D before shriveling. Color: 136B (dark yellowish green) surrounding the female zone.

*Spadix*.—Length: 14.6 cm. Appendix zone: Shape: Lanceolate. Apex: Obtuse. Length: 9.0 cm. Width: 3.3 cm. Color: NN155A (yellowish white). Male zone: Shape: Cylindrical. Length: 2.5 cm. Width: 1.3 cm. Color: N155C (pinkish white). Female zone: Shape: Conical. Length: 3.2 cm. Width: 2.5 cm.

Cold tolerance: Good.

Disease and pest tolerance: Good.

Fruit and seed set: None observed to date.

Drought tolerance: Good.

COMPARISON WITH PARENTAL VARIETIES

'AS12-1' differs from the female parent *Alocasia* plant 'Calidora' in that 'AS12-1' has larger leaves that are broadly ovate to cordate in shape with undulating leaf margins that fold downwards giving the leaf an overall scalloped appearance, whereas leaves of 'Calidora' are flattened with little to no undulating margins. Additionally, 'AS12-1' has mature leaves that are moderate olive green on the adaxial surface, whereas 'Calidora' has mature leaves that are a lighter yellow green on the adaxial surface. 'AS12-1' differs from the male parent species *A. amazonica* in that 'AS12-1' has leaves that are broadly ovate to cordate in shape, whereas leaves of *A. amazonica* are narrowly sagittate in shape. In addition, leaves of 'AS12-1' are more horizontal in orientation, compared to the downwardly nodding leaves of *A. amazonica.*

COMPARISON WITH COMMERCIAL VARIETIES

When 'AS12-1' is compared to the commercial *Alocasia* plant 'AP091520' (U.S. Plant Pat. No. 34,129), leaves of 'AS12-1' are more horizontal in orientation compared to the more vertically upright leaves of 'AP091520'. Additionally, 'AS12-1' has leaves that are more broadly ovate to cordate in shape with undulating leaf margins that fold downwards giving the leaf an overall scalloped appearance, whereas leaves of 'AP091520' are less ovate and more cordate in shape with margins that are more flattened and less undulating in appearance.

We claim:

1. A new and distinct variety of *Alocasia* plant named 'AS12-1', substantially as illustrated and described herein.

* * * * *